United States Patent
Grundig et al.

(10) Patent No.: US 6,221,238 B1
(45) Date of Patent: Apr. 24, 2001

(54) ENZYMATIC-ELECTROCHEMICAL ONE-SHOT AFFINITY SENSOR FOR THE QUANTITATIVE DETERMINATION OF ANALYTES FOR AQUEOUS MEDIA AND AFFINITY ASSAY

(75) Inventors: Bernd Grundig, Leipzig; Ilka Renneberg, Berlin; Beate Strehlitz; Holm Kopinke, both of Leipzig, all of (DE)

(73) Assignees: UFZ-Umweltforschungszentrum Leipzig-Halle GmbH; SENSLAB Gesellschaft zur Entwicklung und Herstellung Bioelektrochemischer Sensoren mbH, both of Leipzig (DE)

( * ) Notice: Subject to any disclaimer, the term of this patent is extended or adjusted under 35 U.S.C. 154(b) by 0 days.

(21) Appl. No.: 09/180,874

(22) PCT Filed: May 16, 1997

(86) PCT No.: PCT/EP97/02518

§ 371 Date: Feb. 16, 1999

§ 102(e) Date: Feb. 16, 1999

(87) PCT Pub. No.: WO97/45738

PCT Pub. Date: Dec. 4, 1997

(30) Foreign Application Priority Data

May 24, 1996 (DE) .............................................. 196 22 458

(51) Int. Cl.[7] .................................................. G01N 27/26

(52) U.S. Cl. ...................................... 205/777.5; 204/403

(58) Field of Search ........................... 204/403; 435/817; 205/777.5

(56) References Cited

U.S. PATENT DOCUMENTS

| 4,145,255 | 3/1979 | Fletcher et al. . |
| 4,376,825 | 3/1983 | Rubenstein et al. . |

FOREIGN PATENT DOCUMENTS

| 2642321 | 3/1977 | (DE) . |
| 4216696A1 | 10/1993 | (DE) . |
| 0125139A2 | 11/1984 | (EP) . |
| 0-223541 | 5/1987 | (EP) . |
| 0241309A2 | 10/1987 | (EP) . |
| 8603837 | 7/1986 | (WO) . |
| WO8604926A1 | 8/1986 | (WO) . |

OTHER PUBLICATIONS

Baymann et al, "Analytical Biochemistry", vol. 199, No. 2, Dec. 1991, pp. 269–274.
Heineman et al., *Analytical Chemistry*, vol. 57, No. 12, pp. 1321A–1331A (Oct. 1995).

(List continued on next page.)

*Primary Examiner*—T. Tung
*Assistant Examiner*—Alex Noguerola
(74) *Attorney, Agent, or Firm*—Birch, Stewart, Kolasch & Birch, LLP.

(57) ABSTRACT

The invention relates to an enzymatic-electrochemical affinity sensor and a one-step affinity assay for the quantitative determination of analytes in aqueous media. More specifically, the invention relates to an enzymatic-electrochemical signal amplification system for a highly sensitive indication of affinity reactions and is particularly suitable in the form of a one-step affinity sensor for in situ analytics. The invention is also directed to the use of phenol oxidase as a marker enzyme for the affine binding partners in an electrochemical affinity sensor or assay, and to the use of an enzyme hydrolyzing phenolic compounds as marker enzyme for the affine binding partners, in combination with a phenol oxidase as catalyst for the amplifying reaction in an electrochemical affinity assay.

31 Claims, 3 Drawing Sheets

OTHER PUBLICATIONS

La Salle et al., *J. Electroanal. Chem.*, vol. 350, pp. 329–335 (1993).

Doyle et al., *Anal. Chem*, vol. 56, pp. 2355–2360 (Nov. 1984).

McNeil et al., *Biosensors*, vol. 3, pp. 199–209 (1987/88).

Duan et al., *Analytical Chemistry*, vol. 66, No. 9, pp. 1369–1377 (May 1994).

Meusel et al., *Biosensors & Bioelectronics*, vol. 10, pp. 577–586 (1995).

Másson et al., *Analytica Chimica Acta*, vol. 304, pp. 353–359 (1995).

Weber et al., *Analytical Letters*, vol. 12(B1), pp. 1–9 (1979).

Di Gleria et al., *Anal. Chem.*, vol. 58, pp. 1203–1205 (1986).

Suzawa et al., *Analytical Chemistry*, vol. 66, No. 22, pp. 3889–3894 (Nov. 1994).

Gyss et al. *Anal. Chem.*, vol. 59, pp. 2350–2355 (1987).

Eggers et al., *Clin. Chem.*, vol. 28/9, pp. 1848–1851 (1982).

Cardosi et al., *Electroanalysis*, vol. 1, pp. 297–304 (1989).

O'Daly et al., *Enzyme Microb. Technol.*, vol. 14, pp. 299–302 (Apr. 1992).

Pritchard et al., *Analytica Chimica Acta*, vol. 310, pp. 251–256 (1995).

Kaläb et al., *Analytica Chimica Acta*, vol. 304, pp. 361–368 (1995).

Wright et al., *Biosensors & Bioelectronics*, vol. 10, pp. 495–500 (1995).

ENZYMATIC-ELECTROCHEMICAL ONE-SHOT AFFINITY SENSOR FOR THE QUANTITATIVE DETERMINATION OF ANALYTES FOR AQUEOUS MEDIA AND AFFINITY ASSAY

The invention relates to an enzymatic-electrochemical affinity sensor and a one-step affinity assay for the quantitative determination of analytes in aqueous media. More specifically, the invention relates to an enzymatic-electrochemical signal amplification system for a highly sensitive indication of affinity reactions and is particularly suitable in the form of a one-step affinity sensor for in situ analytics. The invention is also directed to the use of phenol oxidase as a marker enzyme for the affine binding partners in an electrochemical affinity sensor or assay, and to the use of an enzyme hydrolyzing phenolic compounds as marker enzyme for the affine binding partners, in combination with a phenol oxidase as catalyst for the amplifying reaction in an electrochemical affinity assay.

In order to detect immunochemical reactions or affinity reactions in general, a number of electrochemical or enzymatic-electrochemical indication systems are known which are based on the indication of an electrochemically active marker (Heinemann and Halsall, Anal. Chem. 57 (1985), pp. 1321A–1331A; Patent Specification DE 42 16 696; Le Gal La Salle, J. Electroanal. Chem. 350 (1993), 329–335) or an electrochemically active product of the marker enzyme. Above all, alkaline phosphatase (Doyle et al., Anal. Chem. 56 (1984), pp. 2355–2360; McNeil et al., Biosensors 3 (1987), pp. 199–209; Duan et al., Anal. Chem. 66 (1995), pp. 1369–1377; Meusel et al. Biosens. & Bioelectron. 10 (1995), pp. 577–586) or galactosidase (Masson et al., Anal. Chim. Acta 304 (1995), pp. 353–359) is used as marker enzyme. A variety of other enzymatic-electrochemical indication systems are based on the cyclic regeneration of redox-active reactants.

The most frequently described assays are those where either a redox enzyme or a redox mediator is used as a marker for an antigen or an antibody. Following the corresponding immunochemical reaction, an enzymatic redox reaction sequence is completed by the marker in the presence of the enzyme substrate, wherein a redox mediator, a redox-active prosthetic group of the enzyme, or a redox-active enzymatic co-factor, or a redox-active co-substrate is reduced or oxidized. Using an amperometric redox electrode, the redox system is regenerated directly or via a mediator. The current resulting therefrom depends on the analyte concentration, i.e., the redox-active conjugates which, depending on the analyte, is provided by the immune reaction at just a low concentration, causes a cyclic enzymatic-electrochemical regeneration reaction resulting in an amplified signal generation, with a correspondingly high measurement current. The redox marker may be a component of a homogeneous or a heterogeneous immunoassay or an immunoassay according to the competition, titration or displacement principle.

Weber and Purdy (Anal. Letters 12 (1979), pp. 1–9) have been the first to accomplish a homogeneous immunoassay using ferrocene as redox-active label of an antigen and detect the direct oxidation of the ferrocene conjugate at –500 mV (vs. SCE).

One enzymatic-electrochemical immunoassay (diGleria et al., Anal. Chem. 58 (1986), pp. 1203–1206) also uses ferrocene as antigen label, wherein glucose oxidase is used in the mediated indicator reaction of the antigen-ferrocene conjugate which is displaced from the binding site of the antibody in the presence of analyte and thus, may assume the electron transfer between said oxidase and the electrode.

The perfection of the above enzymatic-electrochemical immunoassays has been described in the Patent Specification EP 125,139. Again, a redox mediator is used as label for the antigen or the antibody. In the publication by Suzawa et al. (Anal. Chem. 66 (1994), pp. 3889–3894), ferrocene is used as multi-label in combination with glucose oxidase. Another well-known immunoassay (Gyss and Bourdillon, Anal. Chem. 59 (1987), pp. 2350–2355) uses glucose oxidase as marker, wherein benzoquinone serves as mediator.

Increasing the sensitivity of amperometric indication systems on the basis of redox enzyme/mediator sequences in immunoassays is the aim of Patent Specification EP 241, 309. Therein, a second electron acceptor (ferricyanide, polyvinylferrocene or Berlin blue) is introduced into the measuring solution or used to modify the electrode surface and accumulate reduction equivalents from the enzymatic glucose oxidation the via hapten-ferrocene conjugate. Following an accumulation period, the amperometric measurement of the electron acceptor is effected, which has been reduced during this accumulation phase.

In the Patent Specification EP 223,541, use is made of redox mediators shifted in negative direction in their formal potential by coupling a phosphate group or a phenol derivative so that, in contrast to their non-derivatized form, no electron transfer from glucose oxidase to the electrode surface via mediator can occur. Ferrocene or dichlorophenol-indophenol are used as mediators. In the presence of a hapten conjugate which has alkaline phosphatase as marker enzyme and results from a competitive reaction with the analyte, cleavage of the derivatizing group occurs so that the mediator may assume the electron transfer between glucose oxidase and the redox electrode. Depending on the concentration of the available marker enzyme-antigen/antibody conjugate, an anodic measurement current will occur.

Furthermore, a measuring system is known (PCT 86/03837) wherein the marker enzyme itself does not catalyze the indicative redox reaction but rather, generates a redox-active "trigger substance" which either may be detected directly by amperometry or completes an enzymatic-electrochemical amplification sequence as a result of its reversible redox behavior. Alkaline phosphatase or β-galactosidase is used as marker enzyme. In the event of alkaline phosphatase, NADP$^+$ is used as "trigger substrate" which is hydrolyzed to NAD$^+$ by elimination of a phosphate group and, as a co-factor in an ethanol/alcohol dehydrogenase/diaphorase, ethanol/alcohol dehydrogenase/ferricyanide, or ethanol/alcohol dehydrogenase/ferrocene/ferricyanide redox electrode sequence, results in the completion of this redox cascade. In analogy, electrochemical-enzymatic assays on the basis of the direct or mediator-coupled indication of the NADH co-factor have been described by Eggers et al. (Clin. Chem. 28/9 (1982), pp. 1848–1851) and Cardosi et al. (Electroanalysis 1 (1989), 297–304). Alternatively, the alkaline phosphatase marker enzyme may be used to cleave the phosphate group of an SH-containing compound which then acts as an electron donor for a glutathione reductase or diaphorase and is regenerated cathodically. In addition, this Patent Specification also describes the use of β-galactosidase as marker enzyme hydrolyzing the p-hydroxyphenyl-β-galactoside. The p-hydroxyquinone having formed serves as substrate for laccase and again, is regenerated cathodically, so that the resulting reduction current is proportional to the concentration of the anti-body/enzyme conjugate.

An enzymatic electrochemical indication system for immunochemical reactions is known from Patent Specification PCT 86/04926, which system has a depolymerase/ligand conjugate and a redox sequence consisting of an oxidoreductase, a mediator and a redox electrode spatially separated from each other by a polymer, or which contains one of the above-mentioned redox components bound in a polymer or incorporated in a polymer. Preferably, a polysaccharide or a liposome matrix is used as polymer, amyloglucosidase, $\alpha$-amylase or phospholipase is used as depolymerase, ferrocene or a ferrocene derivative is used as mediator, and glucose oxidase or glucose dehydrogenase is used as redox enzyme.

The depolymerase used as marker enzyme causes cleavage of monomers from e polymer, which serve as substrates for an oxidoreductase or become diffusible in the form of mediator-coupled monomers so that in either case, an enzymatic-electrochemical reaction is generated. Other possible depolymerase reactions result in liberation of the redox enzyme enclosed in liposomes, or the penetration of a polymer membrane previously having separated the mediator from the redox enzyme. Again, the amperometric current resulting from this redox sequence is proportional to the marker enzyme-ligand conjugate concentration.

Finally, peroxidase-coupled electrochemical-enzymatic immunoassays have been described. A well-known homogeneous electrochemical-enzymatic immunoassay (J. P. O'Daly et al., Enzyme Microb. Technol. 14 (1992) 4, pp. 299–302) uses a ferrocene derivative as label for a hapten which initially is electrochemically inactive as a result of binding of the conjugate to the antibody. In the presence of the analyte, a displacement reaction occurs, and the mediator used as hapten label completes a peroxidase-catalyzed redox reaction generating a reduction current which is proportional to the analyte concentration. In a reverse procedure (Pritchard et al., Anal. Chim. Acta 310 (1995) pp. 251–256), a peroxidase has been used to label antibodies, the label being detected cathodically via ferrocenemonocarboxylic acid according to a multi-step procedure. For a disposable immunosensor used to detect a low molecular weight analyte in a competitive multi-step assay (Kàlab and Sklàdar, Anal. Chim. Acta 304 (1995), pp. 361–368), a peroxidase has been used as enzyme label of the antibody conjugate which, following a competitive reaction within a defined incubation period between the analyte and the hapten immobilized on the electrode surface, and a washing step, is detected at the electrode using hydroguinone. In another well-known publication (Wright et al., Biosens. & Bioelectron. 10 (1995), pp. 495–500), glucose oxidase is used as enzyme label, the reaction product of which (hydrogen peroxide) being generated in the actual indication reaction via a mediator-free peroxidase-carbon electrode produced using screen printing. However, these well-known electrochemical-enzymatic indication systems for immunochemical reactions or affinity reactions suffer from the general drawback of being either excessively expensive or insufficiently sensitive for practical applications.

The invention was therefore based on the object of providing an affinity assay featuring high sensitivity, easy handling, and an electrical quantification of the measured signal. More specifically, it should be suitable in the form of a one-step affinity sensor in the in situ analytics in aqueous media.

According to the invention, said object is accomplished by means of an enzymatic-electrochemical one-step affinity sensor in accordance with claim 1, the preferred embodiments of subclaims 2 through 18, and by means of an affinity assay according to claim 19, and the associated embodiments of subclaims 20 through 25.

In particular, the sensor or assay according to the invention is suitable to detect low molecular weight substances such as pesticides, PCAHs, PCBs, chlorophenols, heavy metal ions, pharmaceuticals, and high molecular weight substances such as peptides, hormones, proteins, nucleic acids, glycoproteins, cell messengers, as well as microorganisms and viruses.

Hence, the invention is particularly useful in the fields of environmental analytics, medical diagnostics, food analytics, and the control of biotechnological processes.

In the meaning of the invention, ligand or receptor mean the affine binding partners, e.g., antigen and antibody in the event of an immunoassay. The enzyme-labelled binding partners are denoted as conjugates, and the enzymes as marker enzymes. The complexes between ligands and receptors will be referred to as affinity complexes, or as complexed conjugates if one of the affine binding partners of the complex is enzyme-labelled.

The signal-amplifying enzymatic-electrochemical system for detecting affinity reactions, which is the essence of the invention, is based on the use of either a ligand labelled with phenol oxidase, which ligand will undergo an affine reaction with receptors, or a receptor labelled with phenol oxidase, which receptor will undergo an affine reaction with modified ligands or the analyte. The phenol oxidase-receptor conjugate or phenol oxidase-ligand conjugate not bound to an immobilized receptor or ligand during the competitive reaction or displaced during the competitive reaction, or the complex formed upon a pseudo-homogeneous binding reaction between the analyte and the phenol oxidase-receptor conjugate will diffuse through solid phases arranged one after another, which consist of diffusible or immobilized phenol oxidase-ligand conjugate or diffusible or immobilized phenol oxidase-receptor conjugate and succeeding diffusion barriers, to a spatially remote redox electrode (3). In the immediate vicinity of the surface, a previously stored enzyme substrate of the phenol oxidase is oxidized by the phenol oxidase of the conjugate or the complexed conjugate to form an electrically active product which is reduced cathodically via the reversibly reduced electron mediator to form a starting substrate of the phenol oxidase. The resulting cyclic substrate regeneration provides a chemical, analyte-proportional current signal amplification which may be quantified using voltammetric methods.

In the case of a hydrolyzing enzyme used as marker enzyme in an analogous fashion, preferably a phosphatase or a galactosidase, phenol oxidase is fixed as a layer 21 in the immediate vicinity of the electrode surface, and an educt resulting from hydrolysis of a hydrolase substrate previously stored in layer 20 is oxidized by the phenol oxidase used as catalytic layer to form an electrically active product and, again via reversibly reduced electron mediator, reduced cathodically to form a starting substrate of the phenol oxidase. The resulting cyclic substrate regeneration provides a chemical, analyte-proportional current signal amplification which may be quantified using voltammetric methods.

In the meaning of the invention, monoclonal or polyclonal antibodies, antibody fragments, lectins, protein A and G, nucleic acids, biological receptors or mixtures thereof are used as receptors. Affine haptens, peptides, heavy metal ion complexes, nucleic acids, carbohydrates, proteins, microorganisms, viruses, or fragments of microorganisms or viruses are used as ligands versus the receptor.

Tyrosinase is preferably used as phenol oxidase. Alkaline phosphatase is particularly preferred as hydrolyzing enzyme. Preferably, phenol, m-cresol, p-cresol, 2,4-xylenol, p-chlorophenol, or catechol are suitable enzyme substrates of the phenol oxidase, which result in generation of a strong signal.

Quinoid redox dyes, quinones, redox-active complex compounds of iron, ruthenium, osmium, cobalt or tungsten, metallocenes, phthalo(yanines, or electrically conductive redox polymers such as polyaniline, polypyrrole, poly-o-phenylenediamine, or polyacetylene are used as electron mediators in the enzymatic electrochemical indication reaction.

The displacement principle is utilized in a first embodiment according to the invention. It is based on the use of either a phenol oxidase-ligand conjugate or a phenol oxidase-receptor conjugate which serves to saturate the binding sites of a corresponding immobilized receptor or immobilized ligand wherein the phenol oxidase is conjugated with a ligand which, compared to the actual analyte, has a substantially lower affinity versus the receptor, or a ligand is used for immobilization to which the phenol oxidase-labelled receptor has a substantially lower affinity compared to the actual analyte. A molecule having a structural relationship to the analyte is used as ligand. In the presence of analyte, the phenol oxidase-ligand conjugate is displaced by same from the binding sites of the immobilized receptor, or the immobilized ligand is displaced by the analyte from the binding sites of the receptor conjugated with phenol oxidase. The displaced phenol oxidase-ligand conjugate or the phenol oxidase-receptor conjugate complexed with analyte will diffuse to the spatially remote electrode surface and undergo a signal-amplifying enzymatic-electrochemical redox reaction in the presence of a phenol oxidase substrate and a redox mediator, which reaction generates an analyte-proportional, voltammetric test signal.

A second embodiment according to the invention is based on a (quasi)homogeneous affinity reaction. In local separation from an immobilized modified ligand, an affine reaction between the analyte and the phenol oxidase-conjugated receptor present in excess will initially occur. When diffusing to the spatially remote redox electrode, the analyte molecules completed with the phenol oxidase-conjugated receptor, and the excess phenol oxidase-conjugated receptor will pass a section having immobilized ligand to which the non-complexed fraction is bound, so that only the analyte-complexed phenol oxidase-conjugated receptor fraction will undergo a signal-amplifying enzymatic-electrochemical redox reaction at the electrode surface in the presence of a phenol oxidase substrate and a redox mediator.

A third embodiment according to the invention implies an initial affine competitive reaction between the analyte and the phenol oxidase-ligand conjugate for the binding sites of an immobilized receptor. The fraction of phenol oxidase-ligand conjugate which has not been bound as a result of analyte complexing with the receptor will diffuse to the spatially remote redox electrode and undergo a signal-amplifying enzymatic-electrochemical redox reaction in the presence of a phenol oxidase substrate and a redox mediator.

Instead of the phenol oxidase in the above-described embodiments according to the invention, a fourth, particularly preferred embodiment of the invention provides a hydrolyzing enzyme as marker enzyme, preferably a phosphatase or a galactosidase. The phenol oxidase, however, is immobilized directly on the redox electrode surface in the form of a catalytically active layer which then, in the presence of a redox mediator, is capable of introducing the hydrolase used as marker enzyme into the enzymatic-electrochemical detection in a signal-amplifying fashion via one of its products of hydrolysis which also is an efficient enzyme substrate of the phenol oxidase.

Ultimately, the phenol oxidase used as marker enzyme is utilized either directly or as a mediating catalytic layer in the presence of a suitable enzyme substrate and a redox mediator in the actual indication reaction at a cathodically polarized redox electrode wherein the phenol oxidase reacts specific enzyme substrates, preferably phenol, m-cresol, p-cresol, 2,4-xylenol, p-chlorophenol, or catechol to form an electrochemically active product which in turn is reduced voltammetrically to a starting substrate for the phenol oxidase by means of a reversible reduced quinoid redox dye, a quinone, a redox-active metal complex or an electrically conductive polymer. That is to say, the regenerated starting substrate is also available for the enzymatic oxidation reaction. Surprisingly, such a cyclic substrate regeneration or chemical signal amplification results in a detection limit which, compared to well-known amperometric detection systems, is decreased by about three orders of magnitude.

The enzymatic-electrochemical one-step affinity sensor according to the invention consists either of a voltammetric measuring chain 22 printed on a planar support strip 1, or of two identical voltammetric measuring chains 22, 23 printed in close proximity on a common support strip, which chains in either design are covered with a sequence of layers each impregnated with various reagents required for the affinity assay according to the invention. In the twin embodiment, one of the two partial sensors on the common support substrate serves as the actual indication system, while the other partial sensor serves as a functional test.

Each of the voltammetric measuring chains of the sensors consists of a redox electrode 3 and an Ag/AgCl pseudo-reference electrode 4 surrounding same, the surface of said redox electrode being modified by a quinoid redox dye, a quinone, a redox-active complex compound of iron, ruthenium, cobalt, osmium, manganese, or tungsten, a metallocene, a phthalocyanine, or an electrically conductive redox polymer such as polyaniline, polypyrrole, poly-o-phenylenediamine, or polyacetylene. The electrodes, including their contact paths 2 for connection to a potentiostate or a manual measuring instrument, and the necessary isolation layer 5 between the contact paths are applied to the planar support strip using screen printing. The modified redox electrode has cathode polarization versus the pseudo-reference electrode.

Directly above the electrodes, multiple consecutive layers are pressed in close contact onto the electrodes by means of a flexible fixing frame 6, 7 made of plastic, which electrodes, in a well-aimed fashion, promote diffusion or capillary forces or inhibit same for a limited period of time by using appropriate porous materials or modifying same. Preferably, cellulose, polysilicates, linear crosslinked hydrogels or a mixture of said materials, optionally provided with additional hydrophilic components, preferably with a polysaccharide, polyalcohol, poly(ether alcohol), or an inorganic salt, are used as materials promoting diffusion or capillary forces, which materials are also provided with appropriate buffer substances. Hydrophobized paper is preferably used as diffusion barrier layer which is to act as such for a limited period of time. In a preferred embodiment, the areas of the layers towards the electrode surface are of a design so as to decrease in order to achieve an efficient accumulation effect.

Towards the measuring medium, the layers are partially covered by a water-impermeable film or membrane 9, preferably made of PTFE, polycarbonate or a rubber compound, which is spaced apart from the cover 8 of a fixing frame by means of an annular porous spacer 10. The fixing frame 6, 7 which includes a cylindrical cavity to accommodate the layers and protects them against lateral penetration of measuring medium has a circular area in its cover 8. Said area preferably has regularly arranged openings to allow entry of the measuring medium, and is smaller in diameter than the film. Immediately following the film which in turn has a smaller diameter than the cylindrical cavity of the fixing frame, a sample-receiving and reservoir layer 11 is arranged, consisting of a material which rapidly absorbs water and has good swellability, preferably a cellulose layer impregnated with a natural or synthetic hydrogel such as agar, gelatin, pectin, dextrin, polyacrylamide, or polyurethane. When applying an aqueous sample, the sample will diffuse through the openings of the fixing frame cover 8 and the annular spacer 10 into the sample-receiving and reservoir layer 11 until the latter, as a result of its swelling and the volume increase associated therewith, will press the film 9 against the inlet openings of the fixing frame cover 8, so that further supply of sample is prevented. In this fashion, a well-defined sample volume is provided.

The sample-receiving and reservoir layer 11 is followed by a layer 12 which either is provided with freely diffusible phenol oxidase-receptor conjugate or phenol oxidase-conjugated modified ligand and is followed by a diffusion-inhibiting layer 13.

In the event of the phenol oxidase-receptor conjugate present in diffusible form, an affine reaction with the analyte occurs, while in the event of the phenol oxidase-ligand conjugate present in diffusible form, the aim merely is homogeneous distribution of the analyte within said layer. In either event, the incubation period will be determined by the period of time required to break through the succeeding diffusion barrier 13.

According to either of these different cases, the next layer 14 contains either a ligand or a receptor immobilized on the solid phase, which layer in turn is followed by a diffusion barrier layer 15. In the first case, the fraction of phenol oxidase-receptor conjugate which failed to bind analyte in the preceding affine reaction will be bound to the immobilized ligand, while the phenol oxidase-receptor conjugate complexed with analyte will diffuse through said layer as soon as the diffusion barrier is penetrated. In the second case, the analyte and the phenol oxidase-ligand conjugate compete for the binding sites of the immobilized receptor. As a result of the higher affinity of the analyte and the limited amount of receptor, the excess fraction of phenol oxidase-ligand conjugate will diffuse further in an analyte-proportional fashion after breaking through the diffusion barrier 15.

In the following last layer 16, either a receptor for the phenol oxidase-receptor conjugate complexed with analyte or a receptor for the phenol oxidase-ligand conjugate is immobilized on the solid phase for accumulation. Said layer 16 is located immediately in front of the electrode surface and is surrounded by a circular layer 18 which is separated by a diffusion barrier 17 and contains the phenol oxidase substrate. Following an incubation period required for accumulating either the phenol oxidase-receptor conjugate complexed with analyte or the phenol oxidase-ligand conjugate complexed with analyte the substrate, after breaking through the diffusion barrier 17, will penetrate into layer 16 in the vicinity of the electrode, and the actual enzymatic-electrochemical indication reaction will take place at the cathodically polarized redox electrode 3 via the redox mediator bound by adsorption, physical occlusion or covalently to the electrode surface 3.

A second embodiment of the enzymatic-electrochemical one-step affinity sensor according to the invention has a layer 19 immediately following the sample-receiving and reservoir layer 11, which includes a receptor or modified ligand immobilized on the solid phase and complexed either with phenol oxidase-ligand conjugate or phenol oxidase-receptor conjugate. Following diffusion of the sample fluid out of the sample-receiving and sample reservoir layer 11, a displacement reaction caused by the analyte takes place, so that either the analyte will bind to the immobilized receptor, displacing the phenol oxidase-ligand conjugate, or the analyte will complex with the phenol oxidase-receptor conjugate previously bound to the immobilized ligand. Again, after breaking through the diffusion barrier 13, the diffusible fraction of either the phenol oxidase-ligand conjugate or the analyte-complexed phenol oxidase-receptor conjugate resulting from the above will diffuse into the layer 16 in the vicinity of the electrode, which layer is designed as already described above.

A third embodiment of the enzymatic electrochemical one-step affinity sensor according to the invention implies the use of a hydrolyzing enzyme as marker enzyme instead of phenol oxidase and, in contrast to the above-described embodiments, has an additional phenol oxidase layer 21 as layer in the vicinity of the electrode, which is directly immobilized on the electrode surface.

The advantages achieved using the enzymatic-electrochemical affinity assay and the associated enzymatic-electrochemical one-step affinity sensor are particularly to be seen in the fact that an extremely sensitive, electrically quantifiable detection can be effected, particularly of small analyte molecules as well, the one-step measuring system free of reagents and separation enabling easy handling.

Another advantage is provided by using two identical and closely adjacent partial sensor arrays on the same support substrate. As a result of the well-defined diffusible analyte concentration which, in contrast to the actual indication array, is contained in the sample-receiving and reservoir layer 11 of the functional test array, the cathodic measured current of this partial sensor will be higher by a defined difference compared to the indication partial sensor. Thus, in addition to the actual analyte determination, it is possible at the same time to effect a functional control during the measuring procedure, augmenting the reliability of measurement.

In the following Examples 1–3 concerning the determination of the 2,4-dinitrophenol (DNP) model analyte, and in Example 4 concerning the determination of IgA, and with reference to FIGS. 1 through 5b, the invention will be illustrated in more detail without limiting it to the above.

EXAMPLE 1

(FIGS. 1, 2)

Figure 1:
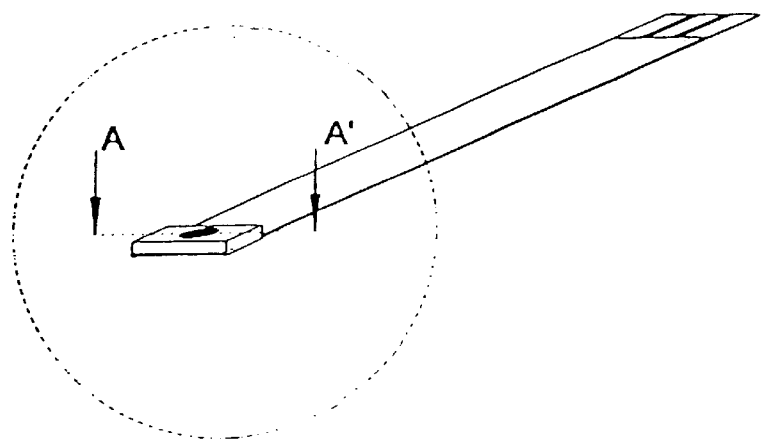
FIG. 1 shows an embodiment of the enzymatic-electrochemical one-step affinity sensor according to the invention in perspective view.
Figure 2:
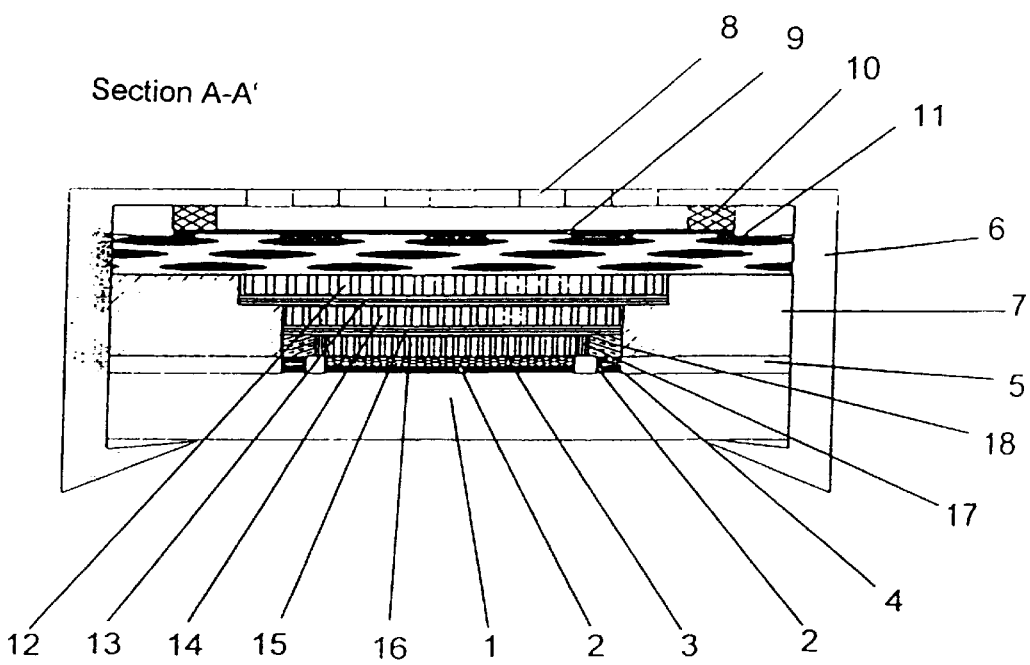
FIG. 2 shows a sectional view along the line A–A' in FIG. 1 of a variant of the enzymatic-electrochemical one-step affinity sensor of the invention according to claim 7.
Figure 3:
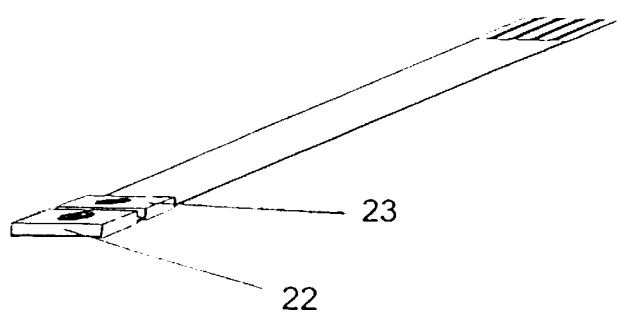
FIG. 3 shows a perspective view of an embodiment of the enzymatic-electrochemical one-step affinity sensor of the invention having a second identical sensor channel on the support to control calibration and function.
Figure 4:
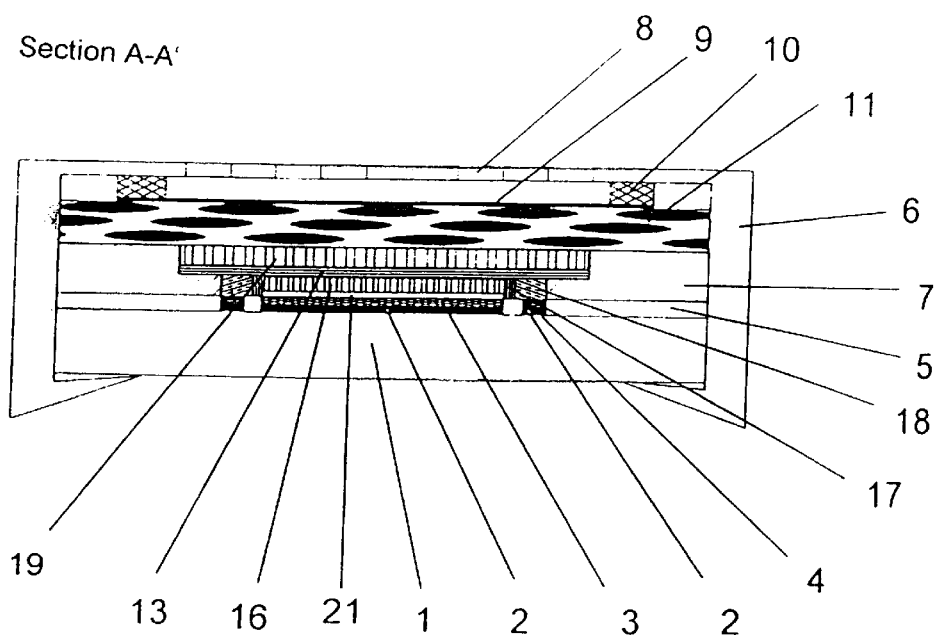
FIG. 4 shows a sectional view along the line A–A' in FIG. 1 of a variant of the enzymatic-electrochemical one-step affinity sensor of the invention according to claim 8.

Carbon contact paths 2, an N-methylphenazinium Reineckate-modified carbon working electrode 3, a silver/silver chloride (Ag/AgCl) reference electrode 4 surrounding the working electrode 3 in the form of a square ribbon, and an isolating layer 5 which, in addition to the surfaces of the working and reference electrodes and plug contact surfaces, covers the support, are printed consecutively on a glass fiber-epoxide resin support 1 using polymer thick-layer pastes and cured at 90° C. Directly on the measuring window surface where the working electrode 3 and the reference electrode 4 are arranged, a fixing frame 6, 7 made of plastic is clamped by appropriate shapings onto the support 1. The fixing frame includes a cylindric cavity and has regularly arranged openings 0.1 mm in diameter in its top cover 8 over a limited circular area 1.5 mm in diameter. The fixing frame is tightly packed with a sequence of different layers: Directly below the perforated circular area of the fixing frame cover 8, there is a Silopren film 9 (ø 3 mm) spaced apart from the cover by an annular spacer 10 (ø 3 mm, $ø_i$ 2 mm) made of filter paper. The Silopren film has been produced by polycondensation through addition of an appropriate catalyst (crosslirker KA-1, Bayer AG) to the Silopren K1000 (Fluka) on a PTFE backing to form a film, and punched out in the form of small plates. The Silopren film is followed by a swellable layer 11 having a diameter of 5 mm, which consists of a filter paper coated with SAN-WET® IM 3900 G (Hoechst AG) and serves as sample-receiving and reservoir layer.

This layer, as well as the next filter paper layers were prepared using Blauband round filter paper (Schleicher & Schull 589/3) previously impregnated with an aqueous solution of 2 vol.-% dextran, m.w. 70,000 (Sigma), 10 vol.-% glycerol, and 0.1 M phosphate buffer, pH 6.8.

The round filter paper had a diameter of 55 mm and was punched out matching to the respective diameter of the cylindrical cavity of the fixing frame (5 mm–1 mm), according to the respective modification procedures.

The sample-receiving and reservoir layer is followed by a filter paper layer 12 (ø 3 mm) containing freely diffusible DNP-L-lysine-tyrosinase conjugate. The ε-2,4-DNP-L-lysine (Sigma) was coupled to tyrosinase, 2000 U/mg (Sigma) in analogy to the mixed anhydride method according to Jung et al., J. Agric. Food Chem. 37 (1989), 1183. Directly below, a slightly hydrophobized paper layer 13 (ø 3 mm) is arranged as diffusion barrier, followed by a filter paper layer 14 (ø 1 mm) having scavenger antibodies immobilized in a directed fashion. To prepare the last-mentioned layer, the filter paper was initially subjected to a hydrolysis procedure. The resulting OH groups were activated using carbonyldiimidazole and covalently bound to the carbohydrates of the Fc portion of the antibodies (2 ml) previously oxidized with periodate, using succinic acid ddhydrazide. For preparation, the well-known procedures were used, such as described in M. B. Wilson and P. K. Nakane: "Immunofluorescence and Related Staining Techniques", Elsevier, North Holland Biomedical Press, pp. 215–224; and in G. T. Eermanson, A. K. Mallia and P. K. Smith: Immobilized Affinity Ligand Techniques, Academic Press, San Diego, Calif., 1992. Commercially available polyclonal anti-DNP antibodies from rabbits (Sigma) were used as antibodies. In order to minimize non-specific binding, the immobilization matrix was blocked with a 1% casein-phosphate buffer/KCl solution.

Again, this is followed by a hydrophobized paper layer 15 (ø 1 mm) and once more by the same filter paper layer 16 (ø 1 mm) having immobilized antibodies, which comes to lie directly on the surface of the working electrode. Said filter paper layer 16 simultaneously forms the space in close vicinity to the electrode and is surrounded by a filter paper ring 18 (ø 2 mm, $ø_i$ 1 mm) impregnated with 0.1 mM catechol, the inner diameter of which is impregnated with silicone, thereby creating a diffusion barrier 17.

When applying a drop of aqueous sample to the perforated fixing frame cover 8, the sample fluid will first diffuse into the sample-receiving and reservoir layer 11 via spacer 9. As a result of swelling of the sample-receiving and reservoir layer 11 caused in this way, the Silopren film 9 is pressed against the Perforated fixing frame cover 8, thus closing same. The aqueous sample diffuses through the succeeding filter paper layer 12 containing dinitrophenol-tyrosinase conjugate, mobilizing the conjugate. After breaking through the hydrophobized paper layer 13 serving as diffusion barrier, both the conjugate and the analyte enter another filter paper layer 14 containing the scavenger antibody immobilized therein. During the heterogeneous immune reaction, the hapten conjugated with tyrosinase and the dinitrophenol will compete for the binding sites of the antibodies immobilized in a directed fashion. Owing to the higher affinity of the analyte molecules versus the conjugate, complexing of the analyte is preferred. The more analyte is present in the sample, the less DNP-L-lysine-tyrosinase conjugate will be bound. A sufficient incubation period for the competitive immune reaction is ensured by the hydrophobic paper layer 15 arranged in succession. Having overcome this diffusion barrier, the non-bound hapten-enzyme conjugate enters the layer 16 in the vicinity of the electrode, which in turn is provided with immobilized antibodies against DNP, and is accumulated directly in front of the electrode surface 3 via binding to said antibodies. Because the sample is an aqueous one, the catechol used as enzyme substrate will be dissolved from the filter paper ring 18 surrounding the layer in the vicinity of the electrode, initiating its enzyme-catalyzed reaction. The catechol is oxidized to o-quinone which is reduced back to catechol by the cathodically reduced N-methylphenazinium on the electrode surface 3. The cathodic measured current resulting from this cyclic enzymatic-electrochemical substrate regeneration, which is detected as peak current using square wave voltammetry at −160 mV versus internal Ag/AgCl pseudo-reference electrode 4, is proportional to the DNP concentration. The measuring range of this one-step immunosensor is between 0.5 and 20 μg/l for DNP.

EXAMPLE 2

Figure 5A:
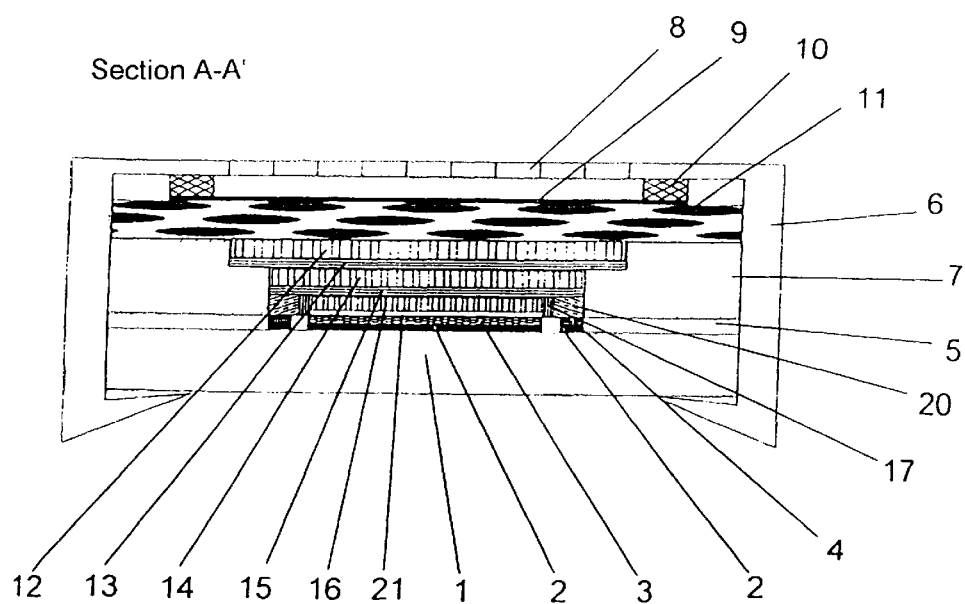
FIG. 5a shows a sectional view along the line A–A' in FIG. 1 of a variant of the enzymatic-electrochemical one-step affinity sensor of the invention according to claim 9.
Figure 5B:
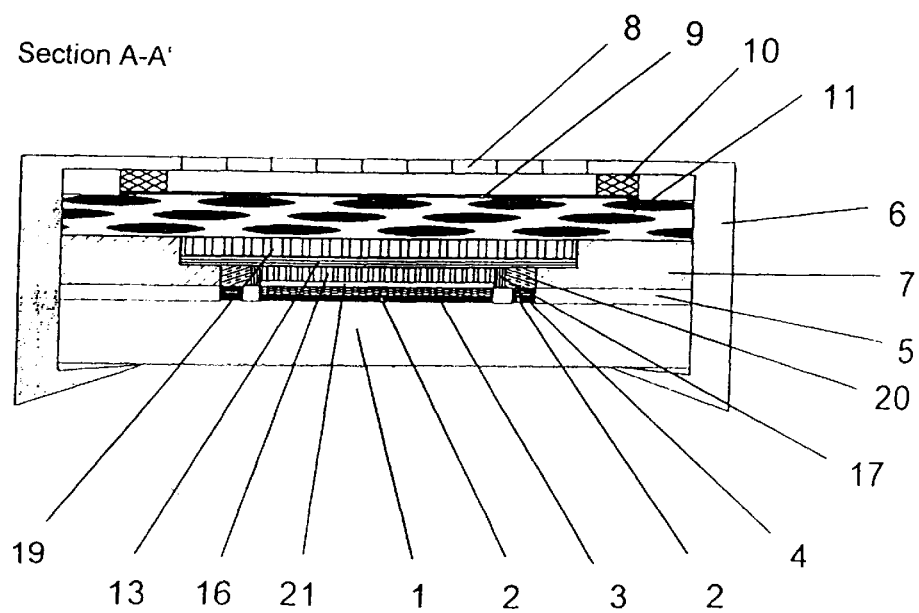
FIG. 5b shows a sectional view along the line A–A' in FIG. 1 of a variant of the enzymatic-electrochemical one-step affinity sensor of the invention according to claim 10.

(FIG. 5a)

The second embodiment is based on the same sensor design as described in Example 1, but uses alkaline phosphatase at 150 U/mg (Sigma) to label the hapten (DNP-L-lysine). Accordingly, the filter paper ring 20 is impregnated with 1 mM phenyl phosphate, and an additional layer 21 containing tyrosinase, 2000 U/mg (Sigma) immobilized in a PUR hydrogel layer (Kotte et al., Anal. Chem. 67 (1995), 65), is inserted between the layer 16 in the vicinity of the electrode and the working electrode surface 3. The immunochemical reaction is analogous to Example 1, the actual indication reaction taking place via the alkaline phosphatase-tyrosinase two-enzyme sequence: The non-bound phosphatase-DNP-L-lysine conjugate which enters the layer 16 in the vicinity of the electrode and is bound by the anti-DNP-antibodies immobilized therein, thus being accumulated, will hydrolyze the phenyl phosphate diffusing out of the surrounding filter paper ring to form phenol. Eventually, the phenol is oxidized by the following tyrosinase layer to form o-quinone which is reduced to catechol by the catholically reduced N-methylphenazinium on the electrode surface 3. The cathodic measured current resulting from this cyclic enzymatic-electrochemical substrate regeneration, which is detected as peak current using square wave voltammetry at −160 mV versus internal Ag/AgCl pseudo-reference electrode 4, is proportional to the DNP concentration. The measuring range of this one-step immunosensor is between 0.1 and 10 μg/l for DNP.

EXAMPLE 3
(FIG. 3)

This example describes the use of two immunosensor systems 22, 23 which are arranged in succession on a support and designed as in Example 1. The actual indication system 22 is constituted by one of the "partial sensors" which function independently, while the other one serves as reference and functional test system 23. The reference and functional test system differs from the indication system in that its sample and reservoir layer is impregnated with a defined analyte concentration of 1 μg/l, so that when applying an appropriate drop of sample or immersing the sensor into the sample, a defined "minimum signal current" can be expected at the reference and control test system 22 as a result of the available analyte, and the actual measured current will add thereto. In the absence of analyte in the sample, said current will be 5 . . . 8 nA. The measured current of the indication system 22 which, depending on the analyte, is between 0.1 and 20 nA, will decrease by said amount of minimum signal current. In this way, not only the sensor function during the actual measuring procedure can be controlled but also, the reliability of the measurement can be increased by accounting for both measured currents during signal evaluation.

EXAMPLE 4
(FIG. 2)

This example describes an affinity sensor on the basis of the lectin jacalin, which is a glycoprotein (Kumar, G. S., et al., Biosci. 4 (1982), 257–61), as selective affine component for the determination of IgA in blood plasma (Kondoh, H., et al., Immunol. Meth. 88 (1986), 171–73). The principal design of the sensor is based on the design described in Example 1. However, freely diffusible IgA-tyrosinase conjugate was used in layer 12. The tyrosinase (Sigma) was coupled to human (plasma) IgA (CALBIOCHEM) in analogy to Example 1. Furthermore, jacalin (Pierce) instead of the scavenger antibody was immobilized in layers 14 and 16. To this end, Blauband round filter paper (Schleicher & Schull 589/3, diameter: 55 mm) was activated using carbonyldiimidazole (Hissey, P. H. et al., Immunol. Meth. 78 (1985), 211–16), so that the jacalin was covalently bound via $NH_2$ groups. 3 mg of jacalin in one milliliter of 0.1 M borate puffer (pH 8.5) was used for a filter paper area of about 23 $cm^2$. For covalent binding, the CDA-activated filter paper was incubated with the jacalin solution for 24 hours at 8° C. and subsequently washed with 0.1 M phosphate buffer solution (pH 6.8) containing 2 vol.-% dextran, m.w. 70,000 (Sigma), 10 vol.-% glycerol (Sigma), and dried. Thereafter, the paper was treated with a 1% casein-phosphate buffer/KCl solution (0.1 M), dried, punched out to a diameter of 1 mm, and used as layers 14 and 16 as described in Example 1.

When applying a drop of blood plasma to the perforated fixing frame cover 8, the sample fluid initially diffuses via spacer 9 into the sample-receiving and reservoir layer 11. As a result of swelling of the sample-receiving and reservoir layer 11 caused in this way, the Silopren film 9 is pressed against the perforated fixing frame cover 8, thus closing same. The aqueous sample will diffuse through the following filter paper layer 12 containing IgA-tyrosinase conjugate, thus mobilizing the conjugate.

After breaking through the hydrophobized paper layer 13 serving as diffusion barrier, both the conjugate and the analyte enter another filter paper layer 14 containing the jacalin immobilized therein. During the heterogeneous immune reaction, the IgA labelled with tyrosinase and the IgA of the sample will compete for the binding sites of the immobilized lectin. Owing to the equilibrium reaction, complexing occurs proportionally to the analyte. The more analyte is present in the sample, the less IgA-tyrosinase conjugate will be bound. A sufficient incubation period for the competitive immune reaction is ensured by the hydrophobic paper layer 15 arranged in succession.

Having overcome this diffusion barrier, the non-bound IgA-enzyme conjugate enters the layer 16 in the vicinity of the electrode which, in an identical manner as layer 14, has immobilized lectin so that the IgA-tyrosinase conjugate not bound in layer 14 now is bound by the immobilized jacalin and thus, is accumulated in front of the electrode surface 3. Because the sample is an aqueous one, the catechol used as enzyme substrate will be dissolved from the filter paper ring 18 surrounding the layer in the vicinity of the electrode, initiating its enzyme-catalyzed reaction. The catechol is oxidized to o-quinone which is reduced back to catechol by the cathodically reduced N-methylphenazinium on the electrode surface 3. The cathodic measured current resulting from this cyclic enzymatic-electrochemical substrate regeneration, which is detected as peak current using square wave voltammetry at −160 mV versus internal Ag/AgCl pseudo-reference electrode 4, is proportional to the IgA concentration.

| Reference Index |   |
|---|---|
| 1 | Support |
| 2 | Contact paths of the electrodes |
| 3 | Mediator-modified redox electrode |
| 4 | Pseudo-reference electrode |
| 5 | Isolating layer |
| 6 | Fixing frame |
| 7 | Fixing frame |
| 8 | Top cover of fixing frame, including perforated area |
| 9 | Film |
| 10 | Spacer |
| 11 | Sample-receiving and reservoir layer |
| 12 | Layer containing freely diffusible ligand or receptor labelled with phenol oxidase or hydrolase |
| 13 | Diffusion barrier layer |
| 14 | Layer containing an immobilized ligand or receptor |
| 15 | Diffusion barrier layer |
| 16 | Layer in the vicinity of the electrode, containing an immobilized ligand or receptor |
| 17 | Diffusion barrier layer |
| 18 | Enzyme substrate layer containing a substrate for phenol oxidase |
| 19 | Layer containing immobilized receptor/ligand complexes labelled with phenol oxidase or hydrolase |

-continued

Reference Index

| | |
|---|---|
| 20 | Enzyme substrate layer containing a substrate for the hydrolase |
| 21 | Layer in the vicinity of the electrode, containing immobilized phenol oxidase |
| 22 | Measuring system (identical with 23) |
| 23 | Measuring system (identical with 22) |

What is claimed is:

1. An enzymatic-electrochemical one-step affinity sensor for the quantitative determination of analytes in aqueous media, comprising a support having applied thereon a measuring system or two adjacent measuring systems of identical design, and the contact paths thereof, wherein each measuring system comprises multiple consecutive layers arranged over a redox electrode modified with an electron mediator, and a pseudo-reference electrode, wherein said layers are laterally encapsulated in a liquid-proof fashion by a fixing frame having a top cover which has an area having openings to receive the sample to be measured, and wherein said layers comprise 1) either
   a) a layer including a phenol oxidase substrate, for that case where a marker enzyme of an affine binding partner is a phenol oxidase, or
   b) a layer including a hydrolase substrate and an additional layer in the vicinity of the electrode which includes immobilized phenol oxidase, for that case where a marker enzyme of an affine binding partner is a hydrolase,
2) a sample-receiving and reservoir layer,
3) a layer in the vicinity of the electrode, and
4)
   a) layers which contain affine binding partners, or
   b) a layer including appropriate immobilized affinity complexes.

2. The sensor according to claim 1, wherein in the event of two measuring systems, one measuring system represents an actual indication system, and the other measuring system is used to control calibration arid test the function of the sensor.

3. The sensor according to claim 1 or 2, wherein the redox electrode has a polarization voltage of between −300 mV and 100 mV versus the pseudo-reference electrode.

4. The sensor according to claim 3, wherein the redox electrode is a mediator-modified carbon electrode and the pseudo-reference electrode is an Ag/AgCl electrode.

5. The sensor according to claim 1, wherein the electron mediator of the modified redox electrode is fixed on the electrode surface by adsorption, physical occlusion, covalent bonding, or in the form of a redox polymer.

6. The sensor according to claim 1, wherein the electron mediator is a quinoid redox dye, a quinone, a redox-active complex compound of iron, ruthenium or tungsten, a metallocene, phthalocyanine, or an electrically conductive redox polymer.

7. The sensor according to claim 1, wherein below the top cover of the fixing frame, a water-impermeable film overlapping the perforations of said cover is arranged, which is spaced apart from said cover by a spacer, and wherein the film is followed by the sample-receiving and reservoir layer.

8. The sensor according to claim 7, wherein the water-impermeable film is a membrane preferably made of PTFE, polyethylene, polycarbonate, or rubber compounds.

9. The sensor according to claim 1, wherein following the sample-receiving and reservoir layer, a layer is arranged which either contains a freely diffusible phenol oxidase-labelled ligand or a freely diffusible phenol oxidase-labelled receptor, followed by a diffusion barrier layer and thereafter, a layer having an immobilized ligand or an immobilized receptor is arranged, followed by a second diffusion barrier layer which is followed by the reaction layer in the vicinity of the electrode as the last layer, to which either the ligand or receptor is immobilized, and which is enclosed by an enzyme substrate layer which is separated by a diffusion barrier and contains a substrate for the phenol oxidase.

10. The sensor according to claim 9, wherein a hydrophobized paper is used as one or more of said diffusion barrier layers.

11. The sensor according to claim 9, wherein the layers containing the affine binding partners, the layers containing the enzyme substrate, the phenol oxidase layer, or the layer containing enzyme-labelled, immobilized affinity complexes comprise an absorbent material containing a hydrophilic component.

12. The sensor according to claim 11, wherein a polysaccharide, a polyalcohol, a poly(ether alcohol), an inorganic salt, or a mixture thereof is used as said hydrophilic component.

13. The sensor according to claim 11, wherein said hydrophilic component of said absorbent material is a cellulose, a polysilicate, a linear-cross-linked hydrogel or a mixture thereof.

14. The sensor according to claim 1, wherein following the sample-receiving and reservoir layer, a layer is arranged which either contains an immobilized receptor complexed with a phenol oxidase-labelled ligand, or an immobilized ligand complexed with a phenol oxidase-labelled receptor, followed by a diffusion barrier layer which is followed by the reaction layer in the vicinity of the electrode as the last layer, to which either the ligand or receptor is immobilized, and which is enclosed by an enzyme substrate layer which is separated by a diffusion barrier and contains a substrate for the phenol oxidase.

15. The sensor according to claim 1, wherein following the sample-receiving and reservoir layer, a layer is arranged that contains a freely diffusible hydrolase-labelled ligand or a freely diffusible hydrolase-labelled receptor, followed by a diffusion barrier layer and thereafter, a layer having an immobilized ligand or an immobilized receptor, followed by a second diffusion barrier layer, followed by the reaction layer in the vicinity of the electrode, to which either the ligand or receptor is immobilized, and which is enclosed by an enzyme substrate layer that is separated by a diffusion barrier and contains a substrate for the hydrolase, followed by an additional layer in the vicinity of the electrode that is arranged between the reaction layer and redox electrode and that contains immobilized phenol oxidase.

16. The sensor according to claim 1, wherein following the sample-receiving and reservoir layer, a layer is arranged which either contains an immobilized receptor complexed with a hydrolase-labelled ligand, or an immobilized ligand complexed with a hydrolase-labelled receptor, followed by a diffusion barrier layer which is followed by the reaction layer in the vicinity of the electrode, to which either the ligand or receptor is immobilized, and which is enclosed by an enzyme substrate layer which is separated by a diffusion barrier and contains a substrate for the hydrolase, followed by an additional layer in the vicinity of the electrode that is arranged between the reaction layer and redox electrode, and that contains immobilized phenol oxidase.

17. The sensor according to claim 1, wherein the sample-receiving and reservoir layer is capable of swelling and contains a natural or synthetic hydrogel.

18. The sensor according to claim 17, wherein said hydrogel comprises agar, gelatin, pectin, dextrin, polyacrylate or polyurethane.

19. The sensor according to claim 1, wherein tyrosinase is used as said phenol oxidase.

20. The sensor according to claim 19, wherein phenol, m-cresol, p-cresol, 2,4-xylenol, p-chlorophenol, or catechol is used as an enzyme substrate of said tyrosinase.

21. The sensor according to claim 1, wherein an alkaline phosphatase, acid phosphatase, or β-galactosidase is used as said hydrolyzing enzyme.

22. The sensor according to claim 1, wherein said electrically conductive redox polymer is polyaniline, polypyrrole, poly-o-phenylenediame or polyacetylene.

23. An enzymatic-electrochemical one-step affinity assay for the quantitative determination of analytes in aqueous media, wherein a
   sample fluid is applied to a perforated area of a fixing frame cover of a sensor according to claim 34, which is connected to a potentiostate or a manual measuring instrument of potentiostatic design; and
   said sample initially, diffuses into the sample-receiving and reservoir layer via the spacer, said layer undergoing swelling, thereby pressing the film against the fixing frame cover, thus closing same, and subsequently, the analyte to be determined in the sample fluid undergoing an affine binding reaction when passing the layers of the sensor, wherein
      a) a phenol oxidase-labelled receptor, a phenol oxidase-labelled ligand, or the corresponding phenol oxidase-labelled affinity complex, together with the analyte, diffuses to a mediator-modified electrode surface, and the phenol oxidase oxidizes a suitable phenol oxidase substrate in the layer in immediate vicinity of the electrode surface to form an electrically active product which is reduced cathodically via the reversibly reduced electron mediator to form a starting substrate of the phenol oxidase, or
      b) a phenol oxidase on a redox electrode is fixed as a layer, and an educt resulting from the reaction of a hydrolyzing enzyme used as label in the same fashion as in a) with a suitable hydrolase substrate is oxidized in the immediate vicinity of the electrode surface by the phenol oxidase used as a catalytic layer to form an electrically active product which is reduced cathodically via the reversibly reduced electron mediator to form a starting substrate of the phenol oxidase; and
   the cyclic substrate regeneration generated in both cases a) or b) resulting in a chemically amplified, analyte-proportional cathodic current which is quantified using per se common voltammetric methods.

24. The assay according to claim 23, wherein the analyte to be determined mobilizes the phenol oxidase-labelled ligand or receptor
   a pseudo-homogeneous binding reaction takes place between the analyte and the diffusible phenol oxidase-labelled receptor or the phenol oxidase-labelled ligand,
   the non-bound fraction of the receptor or ligand conjugate, subsequent to overcoming the diffusion barrier layer is bound to immobilized ligand or immobilized receptor,
   and the analyte receptor conjugate complex or the analyte-ligand conjugate complex, subsequent to overcoming the diffusion barrier layer, enters the reaction layer in the vicinity of the electrode, being bound to an immobilized receptor or ligand, and
   the marker phenol oxidase, after mobilization of the phenol oxidase substrate in the substrate layer and its breaking through the diffusion barrier layer into the reaction-layer in the vicinity of the electrode, catalyzes an amplifying reaction between the phenol oxidase substrate and the modified electrode surface, thus providing an analyte-proportional voltammetric current signal.

25. The assay according to claim 23, wherein the analyte to be determined in the sample fluid mobilizes the phenol oxidase-labelled ligand or receptor,
   the analyte and the phenol oxidase-labelled ligand or the phenol oxidase-labelled receptor, subsequent to overcoming the diffusion barrier layer, compete with immobilized ligand or receptor for the available binding sites, and
   the non-bound phenol oxidase-labelled ligand or phenol oxidase-labelled receptor, subsequent to overcoming the next diffusion barrier layer, enters the reaction layer in the vicinity of the electrode, being bound to an immobilized receptor or ligand, and
   the marker phenol oxidase, after mobilization of the phenol oxidase substrate in the substrate layer and its breaking through the diffusion barrier layer into the reaction layer in the vicinity of the electrode, catalyzes an amplifying reaction between the phenol oxidase substrate and the modified electrode surface, thus providing an analyte-proportional voltammetric current signal.

26. The assay according to claim 23, wherein the analyte to be determined in the sample fluid reaches layer which contains immobilized ligand or receptor, the binding sites thereof being saturated with phenol oxidase-receptor conjugate or phenol oxidase ligand conjugate,
   the analyte displaces part of the phenol oxidase-ligand conjugate or the phenol oxidase receptor conjugate, and
   the phenol oxidase ligand conjugate complexed with analyte or the phenol oxidase receptor conjugate complexed with analyte, subsequent to overcoming the diffusion barrier layer, enters the reaction layer in the vicinity of the electrode, being bound to the receptor or ligand immobilized therein, and
   the marker phenol oxidase, after mobilization of the phenol oxidase substrate in the substrate layer and its breaking through the diffusion barrier layer into the reaction layer in the vicinity of the electrode, catalyzes an amplifying reaction between the phenol oxidase substrate and the modified electrode surface, thus providing an analyte-proportional voltammetric current signal.

27. The assay according to claim 23, wherein the analyte to be determined in the sample fluid mobilizes the hydrolase-labelled receptor or ligand,
   a pseudo-homogeneous binding reaction between the analyte and the diffusible hydrolase-labelled receptor or ligand takes place,
   the non-bound fraction of the receptor conjugate or ligand conjugate, subsequent to overcoming the diffusion barrier layer, is bound to immobilized ligand or receptor in layer, and
   the analyte-receptor conjugate complex or the analyte-ligand conjugate complex, subsequent to overcoming the diffusion barrier layer, enters the reaction layer in the vicinity of the electrode, being bound to an immobilized receptor or ligand, and the marker hydrolase, after mobilization of the hydrolase substrate in the substrate layer and its breaking through the diffusion barrier layer into the reaction layer in the vicinity of the electrode, hydrolyzes an educt which penetrates a layer additionally arranged in front of the electrode surface containing immobilized phenol oxidase and, being a substrate of phenol oxidase, triggers a phenol oxidase-catalyzed amplifying reaction between the phenol oxidase substrate and the modified electrode surface, which provides an analyte-proportional voltammetric current signal.

28. The assay according to claim 23, wherein the analyte to be determined in the sample fluid mobilizes the hydrolase-labelled receptor or ligand, the analyte and the hydrolase-labelled ligand or receptor, subsequent to overcoming the diffusion barrier layer, compete with immobilized ligand or immobilized receptor for the binding sites in layer, and the non-bound fraction of hydrolase-labelled ligand or hydrolase-labelled receptor, subsequent to overcoming the diffusion barrier layer, enters the reaction layer in the vicinity of the electrode, being bound to an immobilized receptor or ligand in said reaction layer, and the marker hydrolase, after mobilization of the hydrolase substrate in the substrate layer and its breaking through the diffusion barrier layer into the reaction layer in the vicinity of the electrode, hydrolyzes an educt which penetrates a layer additionally arranged in front of the electrode surface containing immobilized phenol oxidase and, being a substrate of phenol oxidase, triggers a phenol oxidase-catalyzed amplifying reaction between the phenol oxidase substrate and the modified electrode surface, which provides an analyte-proportional voltammetric current signal.

29. The assay according to claim 23, wherein the analyte to be determined in the sample fluid reaches a layer which contains immobilized ligand or receptor, the binding sites thereof being saturated with hydrolase-receptor conjugate or hydrolase-ligand conjugate, the analyte displaces part of the hydrolase-ligand conjugate or the hydrolase-receptor conjugate, and the hydrolase-ligand conjugate complexed with analyte or the hydrolase-receptor conjugate complexed with analyte, subsequent to overcoming the diffusion barrier layer, enters the reaction layer in the vicinity of the electrode, being bound to the receptor or ligand immobilized therein, and the marker hydrolase, after mobilization of the hydrolase substrate in the substrate layer and its breaking through the diffusion barrier layer into the reaction layer in the vicinity of the electrode, hydrolyzes an educt which penetrates a layer additionally arranged in front of the electrode surface containing immobilized phenol oxidase and, being a substrate of phenol oxidase, triggers a phenol oxidase-catalyzed amplifying reaction between the phenol oxidase substrate and the modified electrode surface, which provides an analyte-proportional voltammetric current signal.

30. A method of determining chemical affinity comprising using a hydrolyzing phenolic compound as a marker enzyme for affine binding partners, and a phenol oxidase as a catalyst for an amplifying reaction between a phenol oxidase substrate and a redox mediator and determining the bond formed between affine partners in an electrochemical assay.

31. The method of claim 30, further comprising employing a phosphatase or galactosidase as said hydrolyzing enzyme, and tyrosinase as said phenol oxidase.

* * * * *